(12) United States Patent
Takemoto et al.

(10) Patent No.: US 10,549,048 B2
(45) Date of Patent: Feb. 4, 2020

(54) SYRINGE ASSEMBLY, SYRINGE ASSEMBLY PACKAGE BODY, SEAL CAP FOR BARREL, AND PREFILLED SYRINGE

(71) Applicant: Terumo Kabushiki Kaisha, Tokyo (JP)

(72) Inventors: Masafumi Takemoto, Shizuoka (JP); Tsuyoshi Yoshimoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 330 days.

(21) Appl. No.: 14/854,655

(22) Filed: Sep. 15, 2015

(65) Prior Publication Data

US 2016/0001006 A1    Jan. 7, 2016

Related U.S. Application Data

(63) Continuation of application No. PCT/JP2013/057420, filed on Mar. 15, 2013.

(51) Int. Cl.
  *A61M 5/32*    (2006.01)
  *A61M 5/00*    (2006.01)
  *A61M 5/28*    (2006.01)

(52) U.S. Cl.
  CPC .......... *A61M 5/3202* (2013.01); *A61M 5/008* (2013.01); *A61M 5/28* (2013.01); *A61M 5/32* (2013.01); *A61M 5/002* (2013.01)

(58) Field of Classification Search
  CPC .... A61M 5/3204; A61M 5/32; A61M 5/3213; A61M 5/3202
  See application file for complete search history.

(56) References Cited

U.S. PATENT DOCUMENTS 6,090,081 A * 7/2000 Sudo ................. A61M 5/31513
                                                604/218
6,551,286 B1   4/2003 Claessens
(Continued)

FOREIGN PATENT DOCUMENTS

DE     9213738 U1 *  3/1993  .......... A61M 5/3202
EP     1 964 586 A1     9/2008
(Continued)

OTHER PUBLICATIONS

Machine translation; description DE9213738, translated on Feb. 22, 2019. (Year: 1992).*
(Continued)

*Primary Examiner* — Nathan R Price
*Assistant Examiner* — Melissa A Snyder
(74) *Attorney, Agent, or Firm* — Foley & Lardner LLP

(57) ABSTRACT

A syringe assembly includes a barrel, and a seal cap mounted to the barrel. The seal cap includes a closed distal end portion, an open proximal end portion, a hollow portion including a barrel end storage portion configured to store a barrel end portion, and a puncture needle storage portion extending from the barrel end storage portion, an insertion allowing portion configured to receive a puncture needle tip of a puncture needle guided to the distal end of the puncture needle storage portion, and a projection portion formed on an inner surface of the barrel end storage portion. The projection portion has a top portion, a distal inclined portion, and a proximal inclined portion extending from the top portion toward the open proximal end portion. A non-stick surface for inhibiting sticking to a barrel end portion of the barrel is formed on an inner surface of the projection portion.

21 Claims, 13 Drawing Sheets

(56) References Cited

U.S. PATENT DOCUMENTS

| | | | |
|---|---|---|---|
| 6,645,635 B2 * | 11/2003 | Muraki | B65D 51/002 |
| | | | 215/364 |
| 6,719,732 B2 | 4/2004 | Courteix | |
| 8,056,719 B2 | 11/2011 | Porret et al. | |
| 8,939,941 B2 * | 1/2015 | Thibault | A61M 5/3202 |
| | | | 604/192 |
| 2002/0062108 A1 | 5/2002 | Courteix | |
| 2007/0250016 A1 | 10/2007 | Pech et al. | |
| 2008/0215013 A1 * | 9/2008 | Felix-Faure | A61M 5/3202 |
| | | | 604/192 |
| 2010/0270197 A1 | 10/2010 | Porret et al. | |
| 2012/0330243 A1 * | 12/2012 | Liversidge | A61M 5/3213 |
| | | | 604/198 |
| 2013/0012886 A1 * | 1/2013 | Kawachi | A61M 5/3202 |
| | | | 604/192 |

FOREIGN PATENT DOCUMENTS

| | | |
|---|---|---|
| EP | 2 548 597 A1 | 1/2013 |
| JP | 2004-513707 A * | 5/2004 |
| JP | 2004-513707 A | 5/2004 |
| JP | 2004-513707 A | 5/2004 |
| JP | 2010-534546 A | 11/2010 |
| JP | 2012-254102 A | 12/2012 |
| JP | 2012-254102 A | 12/2012 |
| WO | WO 02/40063 A1 | 5/2002 |
| WO | WO 2009/016428 A1 | 2/2009 |
| WO | WO-2011/114917 A1 | 9/2011 |

OTHER PUBLICATIONS

International Search Report dated May 28, 2013 issued in PCT/JP2013/057420.

* cited by examiner

SYRINGE ASSEMBLY, SYRINGE ASSEMBLY PACKAGE BODY, SEAL CAP FOR BARREL, AND PREFILLED SYRINGE

CROSS-REFERENCE TO RELATED APPLICATIONS

This application is a continuation application filed under 35 U.S.C. § 111(a) claiming the benefit under 35 U.S.C. §§ 120 and 365(c) of PCT International Application No. PCT/JP2013/057420, filed on Mar. 15, 2013, the contents of which are hereby incorporated by reference in their entirety.

BACKGROUND

Technical Field

The present disclosure relates to a seal cap for a barrel, a syringe assembly to which the seal cap for a barrel is mounted, a prefilled syringe using the syringe assembly to which the seal cap for a barrel is mounted, and a package body storing a plurality of syringe assemblies.

Background Art

A syringe having a puncture needle fixed at a distal end of a barrel has been used as a syringe for administering a low dose of a medical solution, such as an insulin syringe. When a prefilled syringe in which a medical solution is prefilled is provided using a syringe of this type, the tip of the needle needs to be sealed. Such a seal cap for sealing the tip of a needle is proposed, for example, in JP 2010-534546 A ("JP '546"), and U.S. Pat. No. 6,719,732 B2 ("U.S. Pat. No. '732").

A seal cap (shield 10) of JP '546 is configured to cover the distal extremity of a syringe (partially shown on FIG. 2 of JP '546). The distal extremity of the syringe 3 includes a hub 2 on which a needle 6 is fixed. The shield 10 has an open proximal end 11, a closed distal end 12, and a wall 13 extending from the proximal end 11 to the closed distal end 12. The internal face 14 of the wall 13 defines a cavity 15 for receiving the part of the distal extremity of the syringe 3. A portion 14a of the internal face 14 is configured to be in contact with the hub 2 of the distal extremity of the syringe 3 when the shield 10 is secured on the distal end extremity of the syringe in order to protect the distal extremity, for example during transport of an administration device before use.

On FIG. 3 of JP '546, the portion 14a of the internal face 14 of the wall 13 includes a plurality of grooves 16. The grooves 16 are regularly disposed along the circumference of the portion 14a, they are parallel to the longitudinal axes A of the shield 10. They allow air to flow during the assembly of the shield on the hub 2. The sticky surface of the shield is smaller, so the assembly is facilitated, and it is easy to have the respective longitudinal axis A and B (see FIG. 2) of both the shield 10 and the administration device 3 to remain confounded. The shield 10 of the invention is therefore perfectly and accurately secured on the extremity of the administration device 3. Because of the grooves created by the specific roughness of the portion 14a of the internal face 14 of the wall 13, it is then easier to remove the shield 10 from the extremity of the administration device 3 at the time of use of the administration device 3.

A seal cap (a device for protecting the needle of a syringe) of U.S. Pat. No. '732 is an elastic needle cap 20 extending in a longitudinal direction between an open proximal end 22 and a closed distal end 24, as illustrated in FIGS. 1 to 5. The cap 20 has an inner housing 26 delimited by a lateral wall 28 and by an end wall 30. Further, between a first and second portions 40 and 42 of the housing 26, there is provided an annular bead 70 (rib) forming an inner swell at the end of the second portion 42 facing the proximal end 22. In order to improve the deformability of this annular bead 70 and to facilitate the passage of the water vapor under pressure, the annular bead 70 is provided with four slots 72 extending in longitudinal direction.

In JP '546, the internal face of the opening of the seal cap (shield 10) has the plurality of grooves axially extending, and the seal cap is readily mounted to and removed from a barrel. However, since the seal cap is readily removed, when the barrel or the prefilled syringe to which the shield 10 is mounted is manufactured, and when the barrel or the prefilled syringe to which the shield 10 is mounted is transported, the shield 10 is likely to be removed unexpectedly from the barrel. Further, the internal face of the shield 10 is in direct close contact with an external face of a distal end of the barrel, therefore, when the barrel is stored while the shield 10 is mounted on the barrel, the shield 10 may stick to the barrel. Further, when sterilization bringing about a pressure load, such as high-pressure steam sterilization or ethylene oxide gas sterilization, is performed, the shield 10 is pressed against the barrel, so that an area of direct close contact between the internal face of the shield 10 and the external face of the distal end of the barrel is increased, and the shield 10 may be stick to the barrel.

In U.S. Pat. No. '732, the seal cap (elastic needle cap 20) has an inner face including the annular bead 70 (rib) forming an inner swell, and the bead 70 is provided with the four slots 72 extending in the longitudinal direction. Therefore, when a barrel or a prefilled syringe to which the elastic needle cap 20 is mounted is manufactured, and when the barrel or prefilled syringe to which the elastic needle cap 20 is mounted is transferred, unexpected removal of the elastic needle cap 20 from the barrel is unlikely to happen. However, the inner face of the elastic needle cap 20 has a large number of portions making a direct close contact with the outer face of the distal end of the barrel, so that when the barrel is stored while the elastic needle cap 20 is mounted to the barrel, the elastic needle cap 20 may stick to the barrel. Further, when the sterilization bringing about a pressure load, such as high-pressure steam sterilization or ethylene oxide gas sterilization, is performed, the elastic needle cap 20 is pressed against the barrel, so that an area of direct close contact between the inner face of the elastic needle cap 20 and the outer face of the distal end of the barrel is increased, and the elastic needle cap 20 may stick to the barrel.

SUMMARY OF INVENTION

An object of certain embodiments of the present invention is to provide a seal cap for a barrel which is inhibited from being unexpectedly removed from a barrel during a process of manufacturing a barrel or a prefilled syringe to which the seal cap is mounted, and during transportation of the barrel or the prefilled syringe to which the seal cap is mounted, and which prevents sticking between an inner surface of a seal cap and an outer surface of a distal end of the barrel, without a failure in removing the cap, even if the barrel is stored while the seal cap is mounted on the barrel, or even if sterilization bringing about a pressure load, such as high-pressure steam sterilization or ethylene oxide gas sterilization, is selected as a method for sterilizing the barrel to which the seal cap is mounted. Another object of certain embodiments of the present invention is to provide a syringe assembly to which the seal cap for a barrel is mounted, a prefilled syringe using the syringe assembly to which the seal cap for a barrel is mounted, and a package body storing a plurality of syringe assemblies.

In one embodiment, a syringe assembly includes a barrel including a barrel body portion, a cylindrical barrel end portion provided at a distal end of the barrel body portion, the cylindrical barrel end portion having an annular head portion and an annular recessed portion formed at a proximal end of the annular head portion, and a puncture needle having a puncture needle tip at a distal end, the puncture needle having a proximal end fixedly inserted into the barrel end portion, and a seal cap mounted to the barrel, wherein the seal cap includes a closed distal end portion, an open proximal end portion, a hollow portion having a barrel end storage portion positioned distally from the open proximal end portion, the barrel end storage portion storing the barrel end portion, and a puncture needle storage portion extending from a distal end of the barrel end storage portion, the puncture needle storage portion storing the puncture needle, an insertion allowing portion for receiving the insertion of the puncture needle tip of the puncture needle stored in the puncture needle storage portion, and a projection portion formed on the inner surface of the barrel end storage portion, on the inner surface of the barrel end storage portion and/or the outer surface of the barrel end portion, a non-stick surface for inhibiting sticking between the inner surface of the barrel end storage portion and the outer surface of the barrel end portion is formed, and the seal cap is mounted to the barrel end portion of the barrel, the puncture needle tip is inserted into the insertion allowing portion of the seal cap, the projection portion of the seal cap and the annular recessed portion of the barrel end portion are engaged with each other, and the inner surface of the barrel end storage portion and the outer surface of the barrel end portion are in close contact with each other through the non-stick surface.

Further, to solve the above-mentioned problems, a prefilled syringe includes the following.

A prefilled syringe including the syringe assembly, a gasket stored in the barrel body portion, and slidably moved in the barrel body portion in a liquid-tight manner, and a medical solution filled in a space formed by the barrel body portion and the gasket.

In another embodiment, a seal cap for a barrel is provided. The seal cap is mounted to a barrel including a barrel body portion, a cylindrical barrel end portion provided at the distal end of the barrel body portion, the barrel end portion having an annular head portion and an annular recessed portion formed at the proximal end of the annular head portion, and a puncture needle having a puncture needle tip at the distal end, the puncture needle having a proximal end fixedly inserted into the barrel end portion. The seal cap includes a closed distal end portion, an open proximal end portion, a hollow portion including a barrel end storage portion positioned distally from the open proximal end portion, the barrel end storage portion storing the barrel end portion, and a puncture needle storage portion extending from a distal end of the barrel end storage portion, the puncture needle storage portion storing the puncture needle, an insertion allowing portion for receiving the insertion of the puncture needle tip of the puncture needle stored in the puncture needle storage portion, and a projection portion formed on the inner surface of the barrel end storage portion, on the inner surface of the barrel end storage portion, a non-stick surface for inhibiting sticking to an outer surface of the barrel end portion is formed, when the seal cap is mounted to the barrel, the puncture needle tip is inserted into the insertion allowing portion of the seal cap, and when the projection portion and the annular recessed portion is engaged with each other, the inner surface of the barrel end storage portion and the outer surface of the barrel end portion are in close contact with each other through the non-stick surface.

A syringe assembly package body storing a plurality of the syringe assemblies is provided. The package body includes a container body having a top opening and having shape retainability, a barrel holder configured to hold a plurality of the syringe assemblies, a plurality of the syringe assemblies held by the barrel holder, and a releasable, sheet-shaped lid member configured to hermetically seal the top opening of the container body, the package body further including a ventilation portion provided in the container body or the lid member, and having bacterial impermeability and a sterilization gas circulation property, wherein the package body is subjected to high-pressure steam sterilization or ethylene oxide gas sterilization.

DETAILED DESCRIPTION

Figure 1:
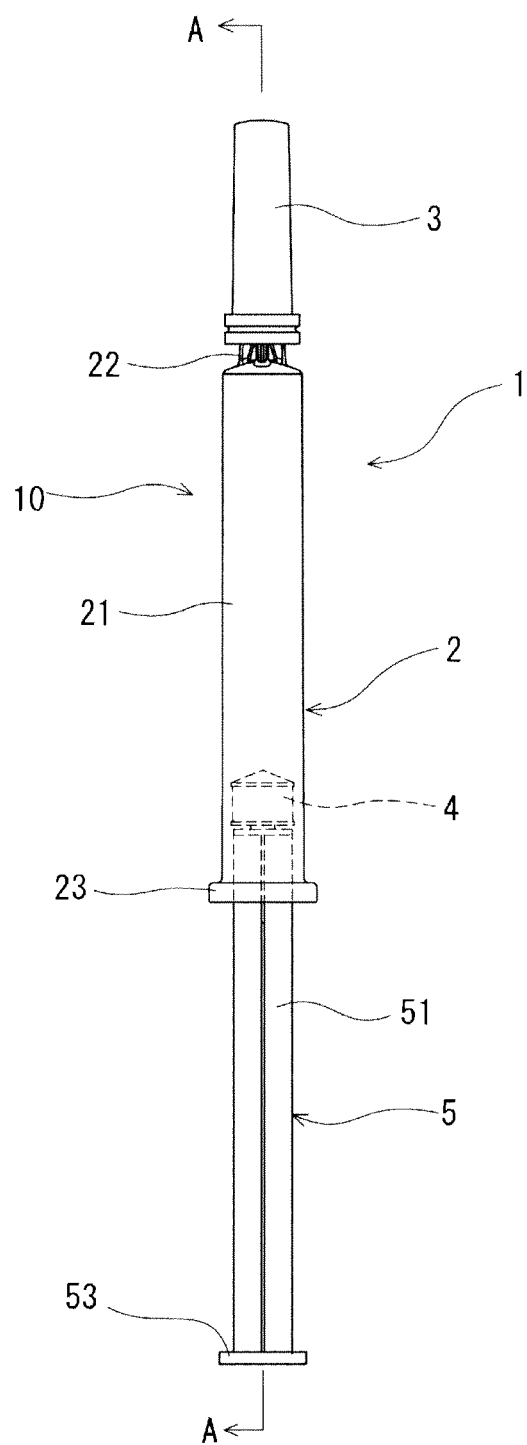
FIG. 1 is a front view of a prefilled syringe according to an embodiment of the present invention.

A seal cap for a barrel, a syringe assembly to which the seal cap for a barrel is mounted, and a prefilled syringe using the syringe assembly to which the seal cap for a barrel is mounted, according to embodiments of the present invention, will be described with reference to the drawings.

The prefilled syringe 1 according to one embodiment of the present invention includes the syringe assembly 10, a gasket 4, and a medical solution 8. The gasket 4 is stored in the syringe assembly 10, and slidably moved in the syringe assembly 10 in a liquid-tight manner. The medical solution 8 is filled in a space formed by the syringe assembly 10 and the gasket 4.

Further, the syringe assembly (i.e., a barrel with a puncture needle to which a cap is mounted) 10 according to an embodiment of the present invention includes a barrel 2, and a seal cap 3 mounted to the barrel 2.

The barrel 2 includes a barrel body portion 21, a cylindrical (hollow) barrel end portion (i.e., puncture needle mounting portion) 22, and the puncture needle 6. The barrel end portion 22 is provided at a distal end of the barrel body portion 21, and has an annular head portion 24 and an annular recessed portion 25 formed at a proximal end of the annular head portion 24. The puncture needle 6 has a puncture needle tip 61 at a distal end, and has a proximal end fixedly inserted into the barrel end portion 22.

The seal cap 3 according to this embodiment of the present invention includes a closed distal end portion 31, an open proximal end portion 32, a hollow portion 30, and a projection portion 36. The hollow portion 30 includes a barrel end storage portion 35 positioned distally from the open proximal end portion 32 and stores the barrel end portion 22, and a puncture needle storage portion 34 extending from a distal end of the barrel end storage portion 35. The insertion allowing portion 33 receives the insertion of the puncture needle tip 61 of the puncture needle 6 stored in the puncture needle storage portion 34. The projection portion 36 is formed on the inner surface of the barrel end storage portion 35. A non-stick surface 9 for inhibiting sticking to a barrel end portion 22 of the barrel 2 is formed on the inner surface of the barrel end storage portion 35.

Further, in the syringe assembly 10 according to an embodiment of the present invention the seal cap 3 is mounted to the distal end of the barrel 2, the puncture needle tip 61 of the puncture needle 6 is inserted into and sealed in the insertion allowing portion 33 of the seal cap 3, the projection portion 36 and the annular recessed portion 25 are engaged with each other, and the inner surface of the barrel end storage portion 35 and the outer surface of the barrel end portion 22 are in close contact with each other through the non-stick surface 9.

Figure 2:
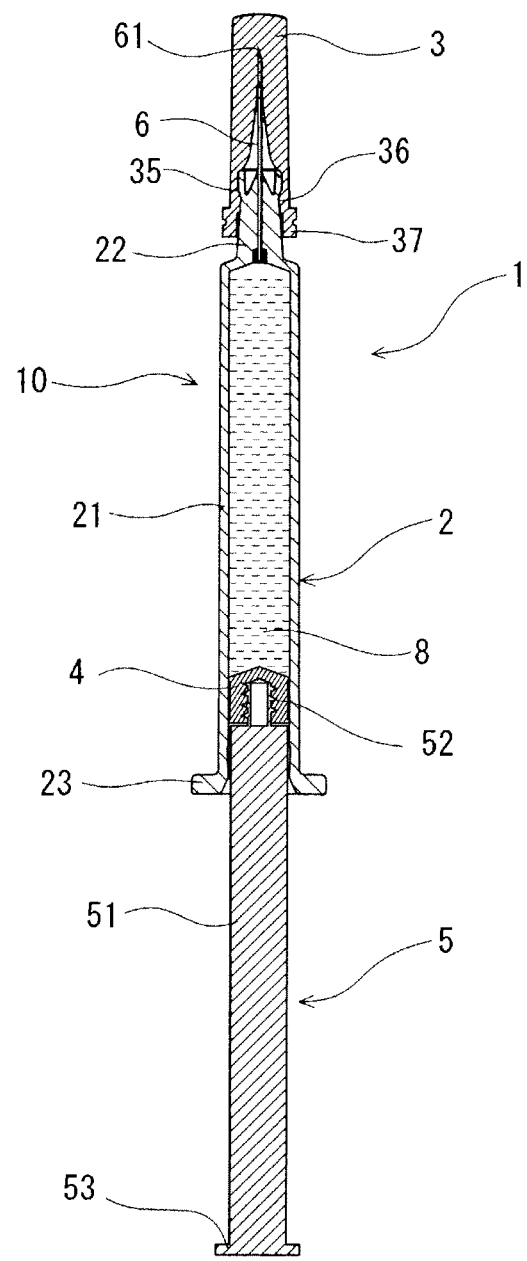
FIG. 2 is a cross-sectional view taken along line A-A of FIG. 1.

As illustrated in FIGS. 1 and 2, the prefilled syringe 1 includes the syringe assembly 10 including the barrel 2, and the seal cap 3 mounted to the barrel 2 to seal the needle tip of the puncture needle, the gasket 4 stored in the syringe assembly 10, and slidably moved in the syringe assembly 10 in the liquid-tight manner, the medical solution 8 filled in the space formed by the syringe assembly 10 and the gasket 4, and a plunger 5 having been mounted to the gasket 4 or to be mounted to the gasket 4 when used.

The medical solution 8 is filled in the space formed by the barrel 2, the gasket 4, and the inside of the seal cap 3.

The medical solution 8 to be filled may include any medical solution, for example, a high concentration sodium chloride injection solution, minerals, a heparin sodium solution, nitroglycerin, an isosorbide dinitrate, a cyclosporine, a benzodiazepine, an antibiotic, a vitamin preparation (multi vitamin preparation), various amino acids, an antithrombotic drug such as heparin, insulin, antitumor drug, an analgesic, a cardiotonic, an intravenous anesthetic, an antiparkinsonism drug, a tumor therapeutic drug, an adrenal corticosteroid, a drug for irregular heartbeat, a correction electrolyte, an antiviral drug, and an immunostimulant.

The barrel 2 includes the barrel body portion 21, the cylindrical (hollow) barrel end portion 22 provided at the distal end of the barrel body portion 21, a flange 23 provided at a proximal end of the barrel body portion 21, and a puncture needle 6 having the proximal end fixedly inserted into the barrel end portion 22. The puncture needle 6 has the puncture needle tip 61 at the distal end. The proximal end of the puncture needle 6 is fixedly inserted into the hollow portion of the barrel end portion 22, and the inside of the puncture needle 6 communicates with an inner space 20 of the barrel 2. It is noted that the puncture needle 6 may be inserted into the hollow portion of the barrel end portion 22 of the barrel 2 previously molded, and may be fixed to the barrel end portion 22 with an adhesive, by thermal welding, or the like. Meanwhile, the puncture needle 6 may be directly fixed to the barrel 2 by insert molding. In the insert molding, when the barrel 2 is molded, the barrel end portion 22 is formed into the cylindrical shape (hollow shape) into which the puncture needle 6 is inserted, and the proximal end of the puncture needle 6 is fixedly inserted into the hollow portion of the barrel end portion 22.

Figure 7:
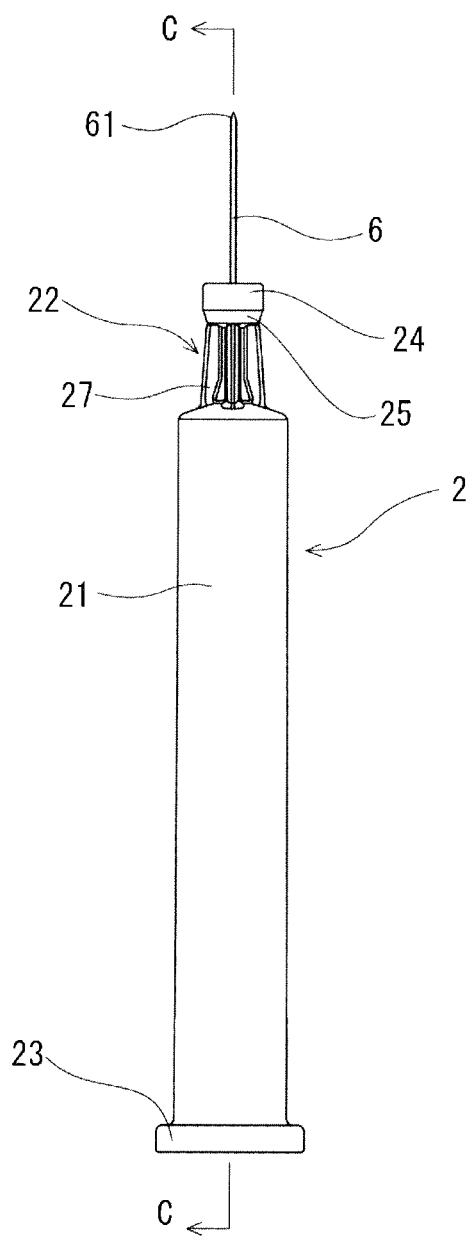
FIG. 7 is a front view of a barrel used for the prefilled syringe of FIGS. 1 and 2 and the syringe assembly of FIG. 3.
Figure 8:
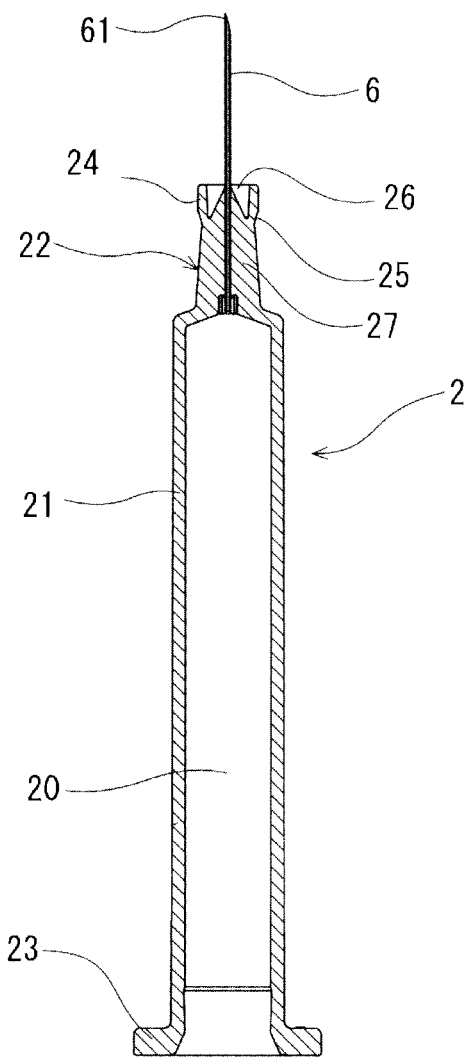
FIG. 8 is an enlarged cross-sectional view taken along line C-C of FIG. 7.
Figure 9:
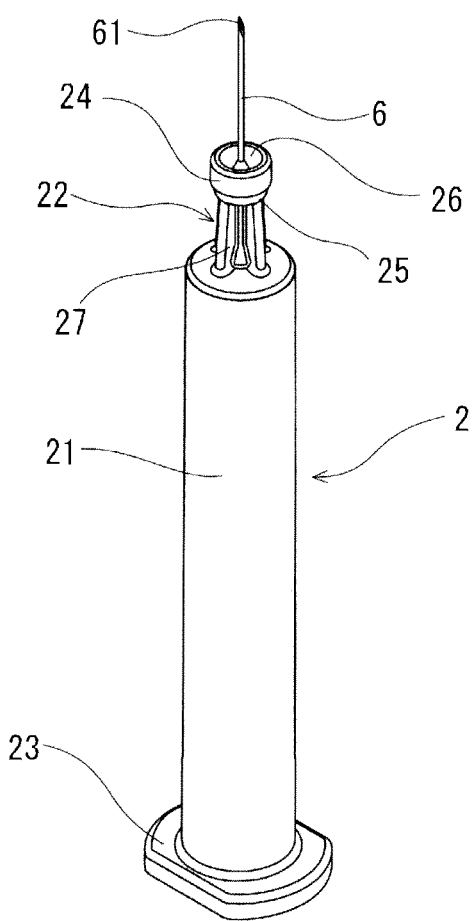
FIG. 9 is a perspective view of the barrel of FIG. 7.

The barrel 2 is transparent or translucent. The barrel body portion 21 is a substantially cylindrical portion storing the gasket 4 to be slidably moved in the liquid-tight manner. The barrel end portion 22 projects forward from the distal end (shoulder portion) of the barrel body portion, and has a hollow cylindrical shape having a diameter smaller than that of the barrel body portion. As illustrated in FIGS. 7 and 8, the barrel end portion 22 has the annular head portion 24 provided at the distal end, a short tapered reduced diameter portion 25 provided at the proximal end of the annular head portion 24, and having a diameter reduced proximally, a connection portion 27 configured to connect a proximal end of the tapered reduced diameter portion 25 and the distal end of the barrel body portion 21, and the annular recessed portion is formed by the tapered reduced diameter portion 25. In the annular head portion 24, a recess 26 recessed proximally from a distal end surface, and a hollow conical portion positioned in the recess 26 and having a top on the distal end side are formed. The connection portion 27 has an outer surface formed with a plurality of grooves extending in an axial direction of the barrel 2. The annular recessed portion may have not the tapered shape but a shape having a diameter only reduced to form a step between the annular recessed portion and the proximal end of the annular head portion 24. The connection portion 27 may be eliminated to directly connect the proximal end of the annular recessed portion (tapered reduced diameter portion 25) and the distal end of the barrel body portion 21. The annular head portion 24 may have a hollow columnar shape (cylindrical shape) from which the recess 26 and the conical portion are eliminated.

A material of the barrel 2 includes a resin, for example, a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, polyester such as a polyethylene terephthalate, a cyclic olefin polymer, and a cyclic olefin copolymer. However, in particular, the resin such as polypropylene, cyclic olefin polymer, or cyclic olefin copolymer is preferably selected, that is because such a resin is readily molded and has heat resistance.

The puncture needle 6 is employed which is hollow and has the puncture needle tip 61 at the distal end. A material of the puncture needle 6 generally includes a metal. The metal preferably includes stainless steel.

As illustrated in FIGS. 1 and 2, the gasket 4 includes a main body portion extending to have substantially the same outer diameter, and a plurality of annular ribs provided at the main body portion (two ribs are employed in the present embodiment, however, when two or more ribs are desired, an appropriate number of ribs may be employed as long as liquid tightness and slidability are satisfied). The ribs make liquid-tight contact with the inner surface of the barrel 2. A distal end surface of the gasket 4 has a shape corresponding to the shape of an inner surface of the distal end of the barrel 2 so that a gap is not formed between the gasket and the barrel as much as possible, when the distal end surface of the gasket abuts on the inner surface of the distal end of the barrel 2.

A material of the gasket 4 preferably includes elastic rubber (e.g., isoprene rubber, butyl rubber, latex rubber, silicone rubber), a synthetic resin (e.g., a styrenic elastomer such as SBS elastomer or SEBS elastomer, or an olefinic elastomer such as ethylene-α-olefin copolymer elastomer), or the like.

The gasket 4 is provided with a recessed portion extending inward from a proximal end of the gasket. The recessed portion is formed as an internal thread to be threadedly engaged with an external thread portion formed on the outer surface of a projection portion 52 formed at a distal end of the plunger 5. The internal and external threads are threadedly engaged, so that the plunger 5 is not removed from the gasket 4. The plunger 5 may be separated usually, and mounted when used. The plunger 5 includes the projection portion 52 projecting forward cylindrically from a disk portion at the distal end, and the outer surface of the projection portion is formed with the external thread threadedly engaged with the recessed portion of the gasket 4. Further, the plunger 5 includes a main body portion 51 having a cross-shaped cross section and extending axially, and a pressure disk portion 53 provided at the proximal end.

The seal cap 3 for a barrel according to this embodiment of the present invention is used by being mounted to the barrel including the barrel body portion 21, the cylindrical barrel end portion 22 provided at the distal end of the barrel body portion 21, and having the annular head portion 24 and the annular recessed portion 25 formed at the proximal end of the annular head portion 24, and the puncture needle 6 having the puncture needle tip 61 at the distal end, and having the proximal end fixedly inserted into the barrel end portion 22.

The seal cap 3 includes the closed distal end portion 31, the open proximal end portion 32, the hollow portion 30 having the barrel end storage portion 35 configured to store the barrel end portion 22, and the puncture needle storage portion 34 extending from the barrel end storage portion 35, the insertion allowing portion 33 configured to receive the insertion of the puncture needle tip 61 of the puncture needle 6 stored in the puncture needle storage portion 34, and the projection portion 36 formed on the inner surface of the barrel end storage portion 35. The non-stick surface 9 for inhibiting sticking to the barrel end portion 22 of the barrel 2 is formed on the inner surface of the barrel end storage portion 35. Therefore, when the seal cap 3 is mounted to the barrel end portion 22 of the barrel 2, the puncture needle tip 61 is inserted into and sealed in the insertion allowing portion 33 of the seal cap 3, further, the projection portion 36 and the annular recessed portion 25 of the barrel end portion 22 of the barrel 2 are engaged with each other, and the inner surface of the barrel end storage portion 35 and the outer surface of the barrel end portion 22 are in close contact with each other through the non-stick surface 9.

Specifically, the seal cap 3 includes the projection portion 36 provided on the inner surface positioned distally by a predetermined length from the open proximal end portion 32. The projection portion 36 has a top portion 36a projecting most, and an inclined portion (tapered portion) 36b extending toward an opening from the top portion 36a, and having a projection height gradually reduced distally. In particular, in the present embodiment, the projection portion 36 is formed as an annular projection portion, and the inclined portion 36b is formed as the tapered portion in which the inner diameter of the barrel end storage portion 35 is reduced distally.

The inner diameter of the barrel end storage portion 35 at the top portion 36a is slightly smaller than the outer diameter at the distal end of the annular recessed portion 25 in the barrel end portion 22 of the barrel 2. Therefore, when the seal cap 3 is mounted to the barrel end portion 22 of the barrel 2, the projection portion 36 and the annular recessed portion 25 are engaged with each other. Further, while the seal cap 3 is mounted to the barrel end portion 22 of the barrel 2, the distal inclined portion 36b extends distally from the annular recessed portion 25. The inner diameter of the barrel end storage portion 35 at least in the vicinity of the proximal end of the distal inclined portion 36b is slightly smaller than the outer diameter of the annular head portion 24 in the barrel end portion 22 of the barrel 2. Therefore, when the seal cap 3 is mounted to the barrel end portion 22 of the barrel 2, the distal inclined portion 36b is hermetically pressed against the outer surface of the annular head portion 24 through the non-stick surface 9, and unexpected removal of the seal cap 3 from the barrel 2 is further reduced.

It is noted that, in the seal cap 3 according to the present embodiment, the inner diameter of the barrel end storage portion 35 at the distal end of the distal inclined portion is slightly smaller than the outer diameter of the annular head portion 24 in the barrel end portion 22 of the barrel 2. Therefore, when the seal cap 3 is mounted to the barrel end portion 22 of the barrel 2, the whole inner surface of the distal inclined portion 36b is hermetically pressed against the outer surface of the annular head portion 24 through the non-stick surface 9. Therefore, the distal inclined portion 36b hermetically pressed against the outer surface of the annular head portion 24 through the non-stick surface 9 has an area increased, and the unexpected removal of the seal cap 3 from the barrel 2 is further reduced.

In the seal cap 3 according to the present embodiment, the projection portion 36 is formed into an annular shape along the inner surface of the barrel end storage portion 35. Therefore, the distal inclined portion 36b hermetically pressed against the outer surface of the annular head portion 24 through the non-stick surface 9 has an area increased, compared with the projection portion 36 intermittently formed on the inner surface of the barrel end storage portion 35, and the unexpected removal of the seal cap 3 from the barrel 2 is further reduced. The projection portion 36 may be formed intermittently on the inner surface of the barrel end storage portion 35.

Further, in the seal cap 3 according to the present embodiment, the projection portion 36 has a proximal inclined portion 36c extending from the top portion 36a toward an opening end (proximal end), and having a projection height gradually reduced toward the opening end (proximal end). Therefore, when the seal cap 3 is mounted to the barrel end portion 22 of the barrel 2, the top portion 36a of the projection portion 36 readily overrides the annular head portion 24 of the barrel end portion 22 from the distal end side.

In particular, in the present embodiment, the projection portion 36 is formed as an annular projection portion, and the proximal inclined portion 36c is formed as a proximal tapered portion in which the inner diameter of the barrel end storage portion 35 is increased proximally. It is noted that, in the seal cap 3 according to the present embodiment, the proximal inclined portion (proximal tapered portion) 36c has a length shorter than and a taper angle larger than the distal inclined portion (distal tapered portion) 36b.

Further, in the seal cap 3 according to the present embodiment, the barrel end storage portion 35 has a linear portion 36d extending distally from the distal end of the distal inclined portion 36b of the projection portion 36 by a predetermined length (specifically, to the proximal end of the puncture needle storage portion 34). In linear portion 36d, the inner diameter of the barrel end storage portion 35 is constant, and is slightly smaller than the outer diameter of the annular head portion 24 in the barrel end portion 22 of the barrel 2. Therefore, when the seal cap 3 is mounted to the barrel end portion 22 of the barrel 2, the linear portion 36d is hermetically pressed against the outer surface of the annular head portion 24 through the non-stick surface 9. In the linear portion 36d, the inner diameter of the barrel end storage portion 35 may be larger than the outer diameter of the annular head portion 24 in the barrel end portion 22 of the barrel 2. Further, the linear portion 36d may be eliminated, and the distal inclined portion 36b may be extended to the proximal end of the puncture needle storage portion 34.

The seal cap 3 preferably has a removal resistance from the barrel 2 of 1.5 to 20 N, especially, 5 to 8 N. Therefore, while the unexpected removal of the seal cap 3 from the barrel 2 is prevented, the seal cap 3 can be readily removed from the barrel 2 when the prefilled syringe 1 is used.

The inclination angle (taper angle) of the distal inclined portion 36b in the projection portion 36 of the seal cap 3 is preferably 1 to 10°, especially, 1 to 6°. Further, the projection height of the top portion of the projection portion 36 is preferably 0.1 to 0.5 mm, especially, 0.05 to 0.25 mm.

In the present embodiment, the proximal end of the distal inclined portion 36b in the projection portion 36 of the seal cap 3 is positioned around the annular recessed portion 25 in the barrel end portion 22 of the barrel 2, and the inner diameter of the barrel end storage portion 35 at least in the vicinity of the proximal end of the distal inclined portion 36b is slightly smaller than the outer diameter of the annular recessed portion 25. Therefore, the distal inclined portion 36b in the projection portion 36 of the seal cap 3 is hermetically pressed against the outer surface of the annular recessed portion 25 through the non-stick surface 9. Therefore, unexpected removal of the seal cap 3 from the barrel 2 is further reduced.

Further, in the present embodiment, the annular recessed portion 25 includes the tapered reduced diameter portion provided at the proximal end of the annular head portion 24, and having a diameter reduced proximally. Therefore, when the seal cap 3 is removed from the barrel 2, the projection portion 36 of the seal cap 3 is pressed and opened outward along the annular recessed portion 25, and readily overrides the annular head portion 24.

The distal inclined portion 36b in the seal cap 3 of the projection portion 36 has a portion hermetically pressed against the outer surface of the annular head portion 24 through the non-stick surface 9, and the portion preferably has a length in the axial direction of the annular head portion 24 of 0.1 to 2.0 mm, especially, 0.3 to 1.5 mm. Therefore, the unexpected removal of the seal cap 3 from the barrel 2 is reduced, and the removal resistance of the seal cap 3 from the barrel 2 is inhibited from being increased more than necessary.

Figure 10:
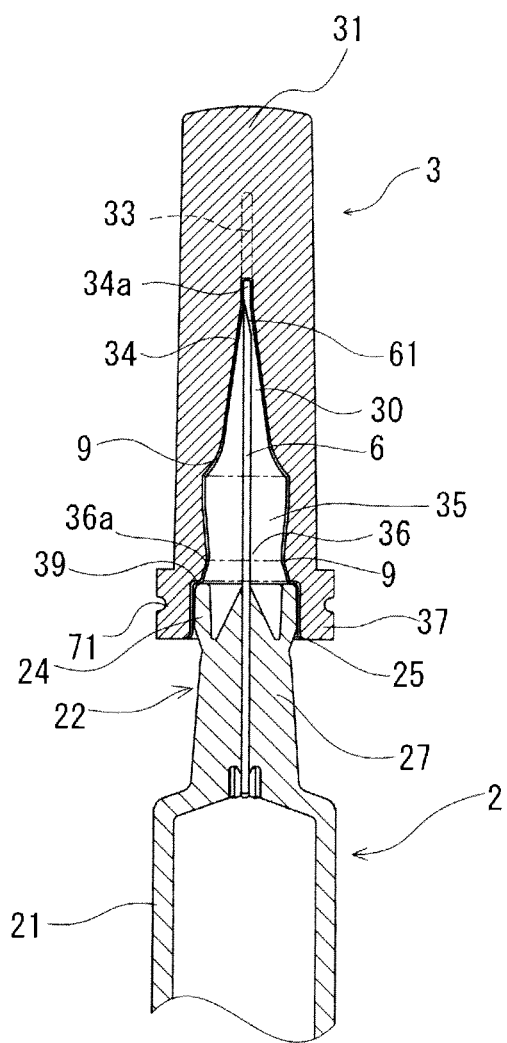
FIG. 10 is a schematic diagram illustrating the function of a seal cap for a barrel according to an embodiment of the present invention.

Further, in the seal cap 3 according to the present embodiment, the hollow portion 30 includes a barrel end introduction portion 38 formed from the open proximal end portion 32 of the seal cap 3 to the proximal end of the barrel end storage portion 35 (projection portion 36), and extending with substantially the same inner diameter. The barrel end introduction portion 38 has an inner diameter slightly larger than the maximum inner diameter of the barrel end storage portion 35, and the inner diameter is slightly larger than the outer diameter of the annular head portion 24 in the barrel end portion 22 of the barrel 2. Therefore, the barrel end introduction portion 38 serves as an introduction portion for the barrel end portion 22 when the seal cap 3 is mounted to the barrel end portion 22 of the barrel 2. Further, the barrel end introduction portion 38 has an annular rising surface 39 rising to be directed toward the open proximal end portion 32, on a boundary with the proximal end of the barrel end storage portion 35 (projection portion 36). Accordingly, when the distal end of the barrel 2 is inserted into the barrel end introduction portion 38 of the seal cap 3, the barrel end portion 22 of the barrel 2 enters the barrel end introduction portion 38, and then an annular distal end surface of the annular head portion 24 of the barrel end portion 22 abuts on the annular rising surface 39 as illustrated in FIG. 10. In this state, the puncture needle 6 is positioned substantially parallel with the axis of the seal cap 3, and is ready to enter a small diameter tip portion 34a of the puncture needle storage portion 34.

It is noted that, when at least the inner diameter of the proximal end is larger than the outer diameter of the annular head portion 24 in the barrel end portion 22 of the barrel 2, the barrel end introduction portion serves as the introduction portion for the barrel end portion 22. Therefore, the inner diameter of the barrel end introduction portion may be reduced distally, different from the above-mentioned embodiment. Further, the annular rising surface 39 may be eliminated from the barrel end introduction portion, and the inner diameter of the barrel end introduction portion may be reduced toward the proximal end of the barrel end storage portion 35 (projection portion 36). Accordingly, when the annular distal end surface of the annular head portion 24 of the barrel end portion 22 enters up to the boundary between the proximal end of the barrel end storage portion 35 (projection portion 36) and the barrel end introduction portion, the puncture needle 6 is positioned substantially parallel with the axis of the seal cap 3, and enters the small diameter tip portion 34a of the puncture needle storage portion 34.

In the seal cap 3 according to the present embodiment, the puncture needle storage portion 34 has a proximal end positioned at the distal end of the linear portion 36d of the barrel end storage portion 35, and has an inner diameter sharply reduced distally. Further, the proximal end of the puncture needle storage portion 34 is formed as a curved annular surface being curved inward to prevent the insertion of the puncture needle 6, and securely guide the puncture needle 6 distally. A main body portion (center part) of the puncture needle storage portion is formed as the tapered portion having a diameter reduced distally, and the small diameter tip portion 34a having an inner diameter slightly larger than the outer diameter of the puncture needle 6, and extending with substantially the same inner diameter is formed at a distal end. As illustrated in FIG. 10, the seal cap according to the present embodiment is configured such that, while the barrel end portion 22 of the barrel 2 is inserted into the seal cap, and the annular distal end surface of the annular head portion 24 of the barrel end portion 22 abuts on the annular rising surface 39 in the barrel end introduction portion 38 of the seal cap 3, the puncture needle tip 61 of the puncture needle 6 enters the small diameter tip portion 34a of the puncture needle storage portion 34, but does not reach the insertion allowing portion 33. The insertion allowing portion 33 is positioned forward (distally) from the barrel end introduction portion 38, to be precise forward from and on the extension of the small diameter tip portion 34a of the puncture needle storage portion 34. The shape of the puncture needle storage portion 34 is not particularly limited as long as the puncture needle 6 can be stored, and may be for example a mere cylinder.

Figure 6:
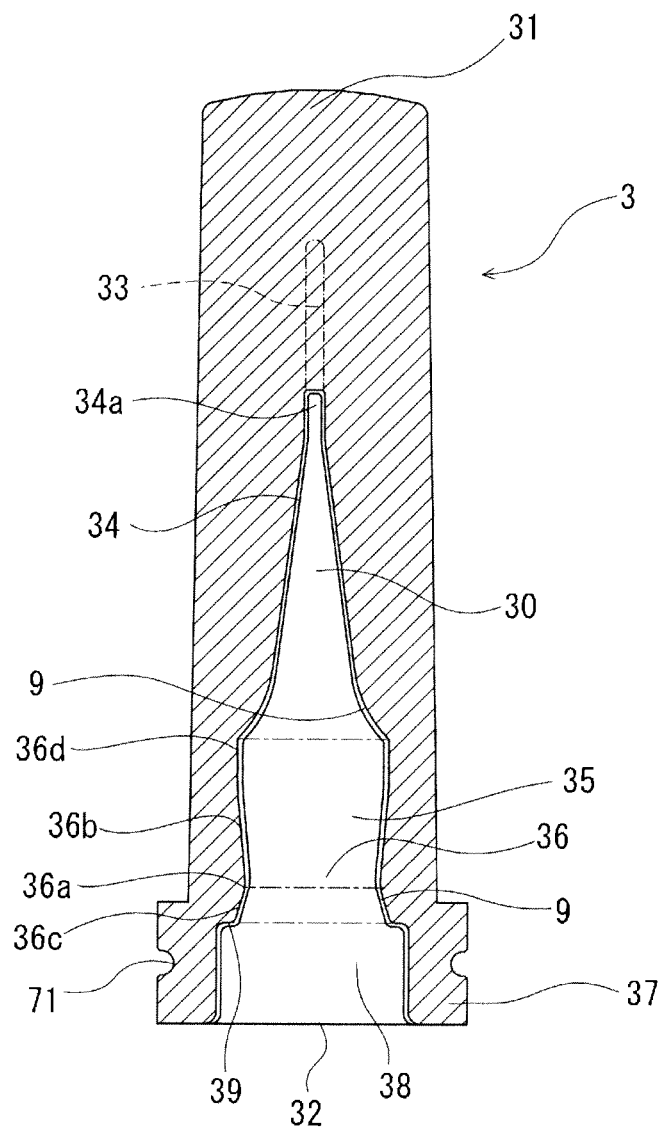
FIG. 6 is an enlarged cross-sectional view taken along line B-B of FIG. 4.

Further, the proximal end of the seal cap 3 is formed with a flange 37 for gripping, projecting annularly outward, and the flange 37 is provided with an annular recessed portion 71. The distal end side of the flange 37 is positioned distally from the annular rising surface 39 of the hollow portion 30, and near the top portion 36a of the projection portion 36 (slightly on the open proximal end portion 32 side from the top portion 36a, in FIG. 6).

For a material of the seal cap 3, at least the insertion allowing portion 33 needs to include an elastic material allowing the insertion of the puncture needle. The elastic material into which the puncture needle can be inserted preferably includes, for example, rubber such as butyl rubber, isoprene rubber, latex rubber, silicone rubber, or an elastomer such as a synthetic resin elastomer (e.g., a styrenic elastomer such as SBS elastomer or SEBS elastomer, or an olefinic elastomer such as ethylene-α-olefin copolymer elastomer. In the seal cap 3 according to the present embodiment, at least the barrel end storage portion 35 and the insertion allowing portion 33 (whole of the seal cap in the present embodiment) include the elastic material into which the puncture needle can be inserted. Therefore, when the seal cap 3 is mounted to the barrel end portion 22 of the barrel 2, the inner surface of the barrel end storage portion 35 is elastically deformed following the outer surface of the annular head portion 24 of the barrel end portion 22. Accordingly, the inner surface of the barrel end storage portion 35 and the outer surface of the annular head portion 24 of the barrel end portion 22 are brought into closer contact with each other through the non-stick surface 9, and the unexpected removal of the seal cap 3 from the barrel 2 is further reduced. For the seal cap 3, only the insertion allowing portion 33 or the vicinity thereof may include the elastic material into which the puncture needle can be inserted, and the outside of the insertion allowing portion 33 may include a hard or semi-hard material. A material of the outside portion of the seal cap includes, for example, a resin such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester such as polyethylene terephthalate, or a cyclic polyolefin. In the seal cap, at least the barrel end storage portion and the insertion allowing portion may include the above-mentioned elastic material into which the puncture needle can be inserted, and the outside of the those portion may be at least partially covered with a cover member including the above-mentioned hard or semi-hard material.

The non-stick surface 9 for inhibiting sticking to the outer surface of the barrel end portion 22 of the barrel 2 is formed on at least the inner surface of the barrel end storage portion 35 of the seal cap 3. It is noted that the non-stick surface 9 may be formed not over the whole of the inner surface of the barrel end storage portion 35, but only at a portion making close contact with the outer surface of the barrel end portion 22. The non-stick surface 9 is preferably formed by, for example, a coating of a non-stick substance and/or a surface treatment imparting non-adhesiveness to a portion being the non-stick surface. The coating of a non-stick substance includes, for example, applying a non-stick polymer film or a liquid substance imparting non-sticky (e.g., liquid silicone oil). The surface treatment imparting non-adhesiveness includes, for example, epoxidation or halogenation. In particular, the non-stick polymer film hardly deteriorates with time, hardly interacts with the medical solution 8 filled in the barrel 2 (e.g., adsorption of the medical solution), and is particularly preferable as the non-stick surface. Further, it is preferable that the non-stick polymer film has compatibility or adhesiveness with a material forming the inner surface of the hollow portion 30 of the seal cap 3, and is not separated from the material.

The non-stick polymer film includes a fluorine resin such as polytetrafluoroethylene (PTFE), tetrafluoroethylene/perfluoalkylvinylether copolymer resin (PFA), tetrafluoroethylene/hexafluoropropylene copolymer (FEP), polychlorotrifluoroethylene (PCTFE), or polyvinylidene difluoride (PVDF), a silicon resin such as silicone polymer film formed from a liquid coating agent consisting primarily of a reactive silicone oil, polyparaxylene, diamond like carbon, or the like.

Especially, the non-stick polymer film is preferably a silicone polymer film formed from a liquid coating agent consisting primarily of a reactive silicone oil. Since the liquid coating agent consisting primarily of a reactive silicone oil is a liquid, the non-stick substance can be readily and accurately applied to an inner surface of the seal cap 3 (barrel end storage portion 35), and since the liquid coating agent is copolymerized (including cross-linking) at normal temperature or by heat to form the silicone polymer film, the non-stick polymer film can be readily and accurately formed on the inner surface of the seal cap 3 (barrel end storage portion 35). In addition, the polymer film of the reactive silicone oil which is formed from the liquid coating agent consisting primarily of a reactive silicone oil has elasticity, so that, when the seal cap 3 is mounted to the barrel end portion 22 of the barrel 2, even if the inner surface of the seal cap 3 (barrel end storage portion 35) is deformed to be pressed outward by the annular head portion 24 of the barrel end portion 22, the polymer film follows the deformation, and is hardly separated from the inner surface of the seal cap 3 (barrel end storage portion 35).

Specifically, the reactive silicone oil includes a polydimethylsiloxane having a functional group at either end, the functional group including a silanol group, amino group, epoxy group, alicyclic epoxy group, carbinol group, methacrylate group, polyether group, mercapto group, carboxyl group, or phenolic group. In particular, a polydimethylsiloxane having the silanol groups at both ends is preferably employed. When the polysiloxane having the silanol groups at both ends is employed, a reactive silicone oil condensate thereof has chemically stable siloxane bond in the main chain, and can form a silicone polymer film hardly interacting with the medical solution 8 filled in the barrel 2 (e.g., adsorption of the medical solution).

In the seal cap 3 according to the present embodiment, the non-stick surface 9 is also formed on an inner surface of the puncture needle storage portion 34. Therefore, even if the puncture needle tip 61 of the puncture needle 6 makes contact with the inner surface of the puncture needle storage portion 34, the puncture needle tip 61 does not stick to the inner surface of the puncture needle storage portion 34. Accordingly, when the seal cap 3 is mounted to the barrel end portion 22 of the barrel 2, the puncture needle tip 61 of the puncture needle 6 entering the puncture needle storage portion 34 is guided to the distal end (small diameter tip portion 34a) of the puncture needle storage portion 34, without sticking to the inner surface of the puncture needle storage portion 34, and accurately inserted into the insertion allowing portion 33.

Further, in the seal cap 3 according to the present embodiment, the non-stick surface 9 is also formed on an inner surface of the barrel end introduction portion 38. Therefore, when the barrel end portion 22 enters the barrel end introduction portion 38, the outer surface of the barrel end portion 22 does not stick to the inner surface of the barrel end introduction portion 38. Thus, the seal cap 3 can be smoothly mounted to the barrel end portion 22 of the barrel 2.

Figure 3:
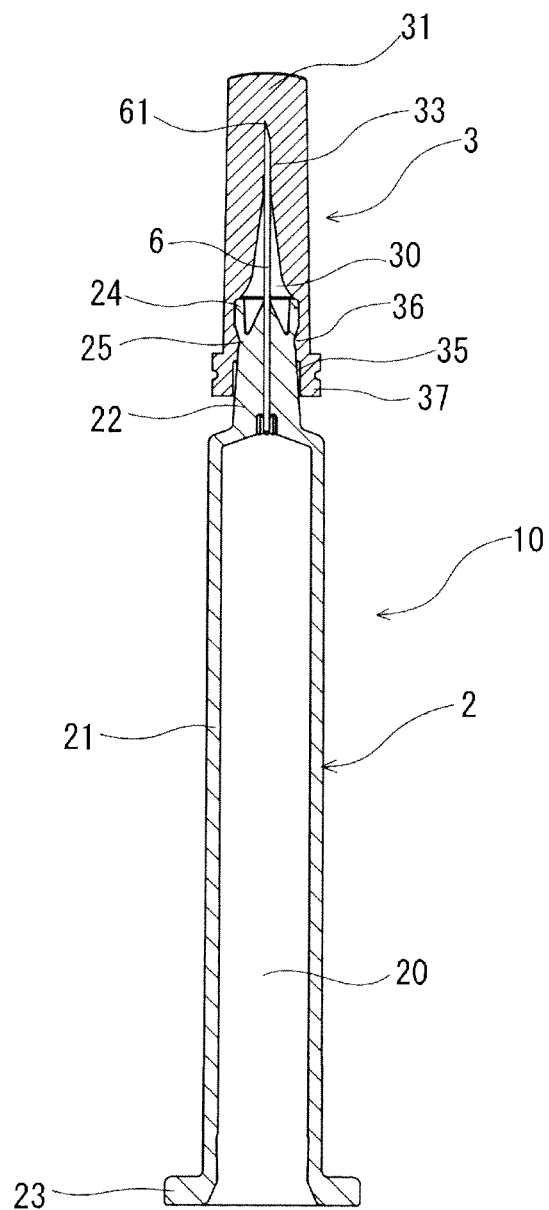
FIG. 3 is an enlarged cross-sectional view of a syringe assembly of an embodiment of the present invention used for the prefilled syringe of FIGS. 1 and 2.
Figure 4:
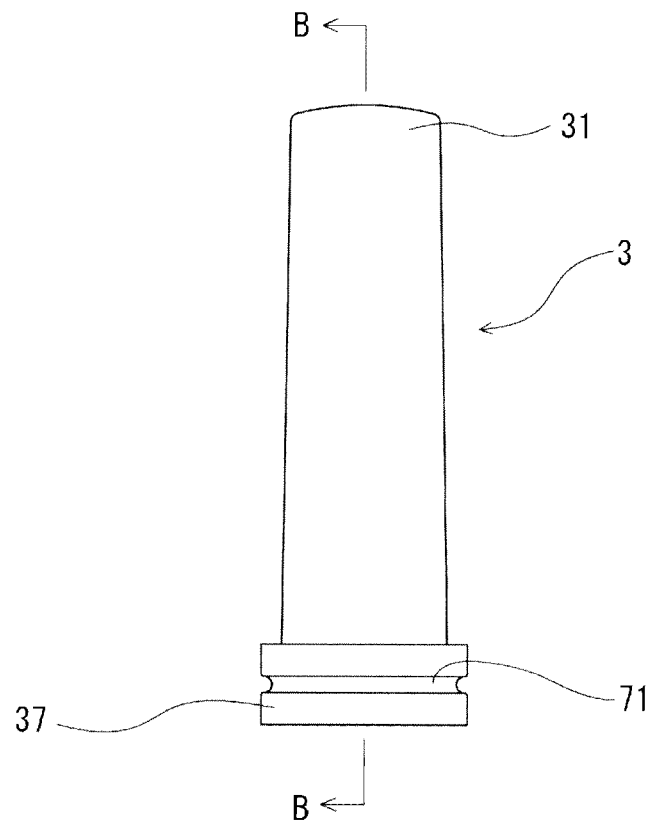
FIG. 4 is an enlarged front view of a seal cap for a barrel according to an embodiment of the present invention used for the prefilled syringe of FIGS. 1 and 2 and the syringe assembly of FIG. 3.
Figure 5:
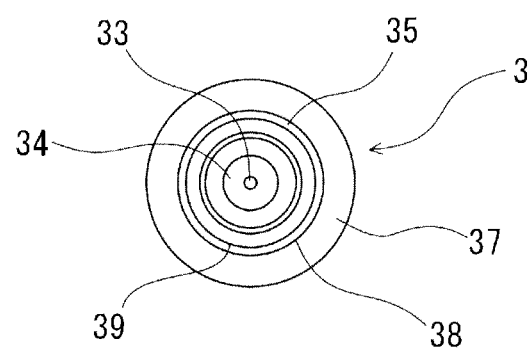
FIG. 5 is a bottom view of the seal cap for a barrel of FIG. 4.

As illustrated in FIG. 3, in the syringe assembly 10 according to an embodiment of the present invention the seal cap 3 is mounted to the distal end (barrel end portion 22) of the barrel 2, the puncture needle tip 61 of the puncture needle 6 is inserted into the insertion allowing portion 33 of the seal cap 3 and sealed in the liquid-tight manner, the annular recessed portion 25 of the barrel end portion 22 and the projection portion 36 formed on the inner surface of the barrel end storage portion 35 are engaged with each other, and the inner surface of the barrel end storage portion 35 and the outer surface of the barrel end portion 22 are in close contact with each other through the non-stick surface 9.

In the syringe assembly 10, the inner surface of the barrel end storage portion 35 and the outer surface of the barrel end portion 22 are in close contact with each other through the non-stick surface 9, so that, even if the barrel 2 is stored while the seal cap 3 is mounted on the barrel 2, and even if sterilization bringing about a pressure load is performed, such as high-pressure steam sterilization or ethylene oxide gas sterilization, the sticking between the inner surface of the barrel end storage portion 35 and the outer surface of the barrel end portion 22 can be inhibited. Similarly, in the prefilled syringe 1 according to an embodiment of the present invention, the inner surface of the barrel end storage portion 35 and the outer surface of the barrel end portion 22 are in close contact with each other through the non-stick surface 9, so that, even if the barrel 2 is stored while the seal cap 3 is mounted on the barrel 2, and even if sterilization bringing about a pressure load, such as high-pressure steam sterilization or ethylene oxide gas sterilization, is performed, the sticking between the inner surface of the barrel end storage portion 35 and the outer surface of the barrel end portion 22 can be inhibited.

In the embodiment described above, the non-stick surface 9 is formed on the inner surface of the barrel end storage portion 35, but the non-stick surface 9 is not limited to be formed on the inner surface of the barrel end storage portion 35, and the non-stick surface may be formed on the outer surface of the barrel end portion. Further, the non-stick surface may be formed on both of the inner surface of the barrel end storage portion and the outer surface of the barrel end storage portion.

Next, an a package body storing a plurality of the syringe assemblies according to an embodiment of the present invention will be described with reference to FIGS. 11 to 15.

A sterilizable or sterilized prefilled syringe assembly package body 100 storing a plurality of the syringe assemblies according to the embodiment of the present invention includes a container body 102, a barrel holder 104, the plurality of the syringe assemblies 10, and a sheet-shaped lid member 103. The container body 102 has a top opening and has shape retainability. The barrel holder 104 holds the plurality of the syringe assemblies 10 stored in the container body 102. The plurality of the syringe assemblies 10 is held by the barrel holder 104. The sheet-shaped lid member 103 releasably hermetically seals the top opening of the container body 102.

The prefilled syringe assembly package body 100 according to the embodiment of the present invention employs a sterilizable or sterilized prefilled syringe assembly package body. A sterilization method includes high-pressure steam sterilization, radiation or electron beam sterilization, or ethylene oxide gas sterilization.

Figure 11:
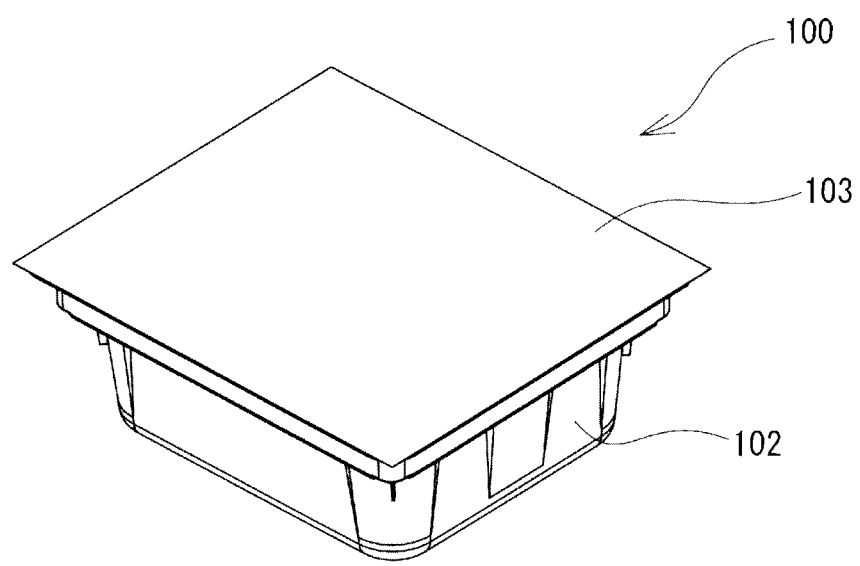
FIG. 11 is a perspective view of a syringe assembly package body according to an embodiment of the present invention.
Figure 12:
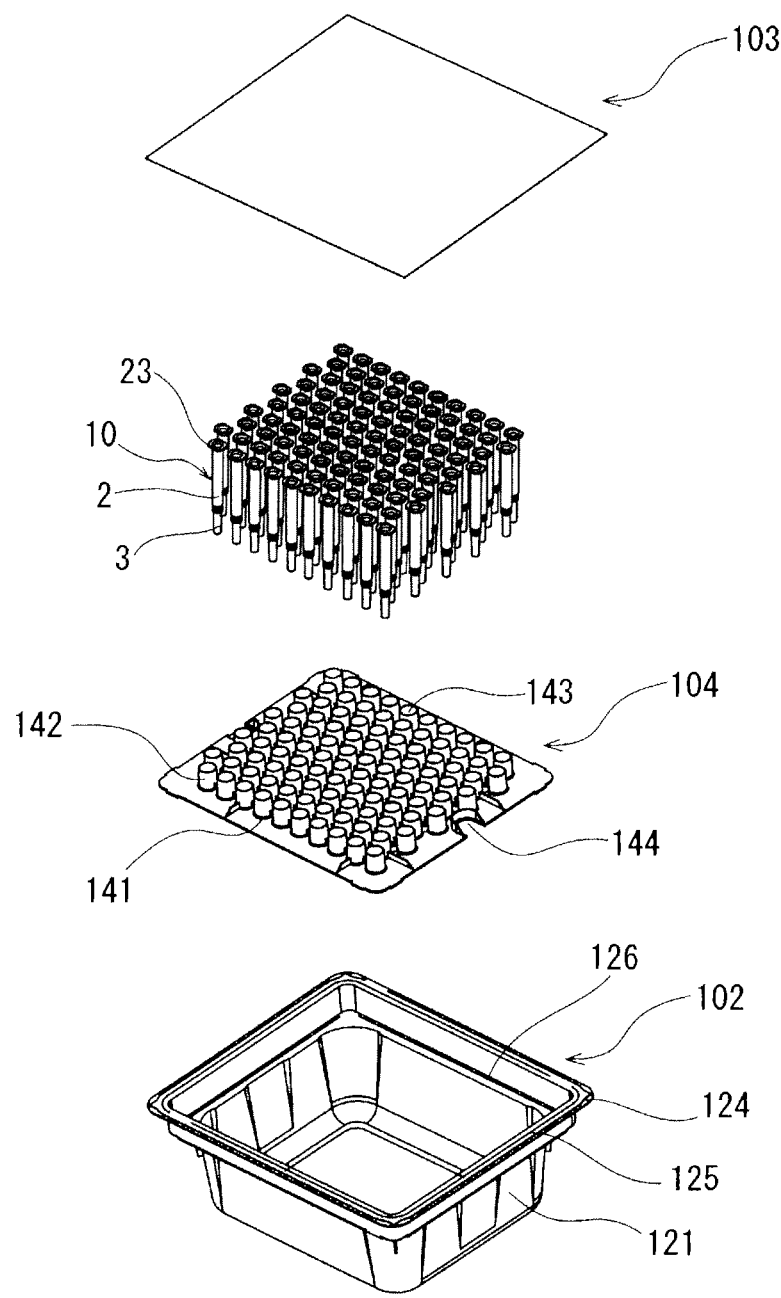
FIG. 12 is a schematic diagram illustrating an inner mode of the syringe assembly package body of FIG. 11.
Figure 13:
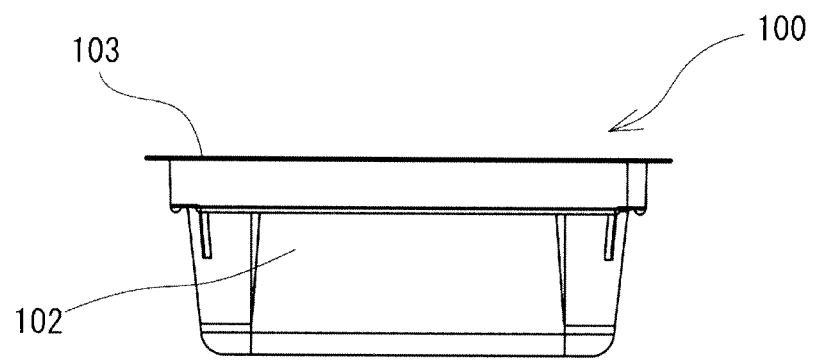
FIG. 13 is a front view of the syringe assembly package body of FIG. 11.
Figure 14:
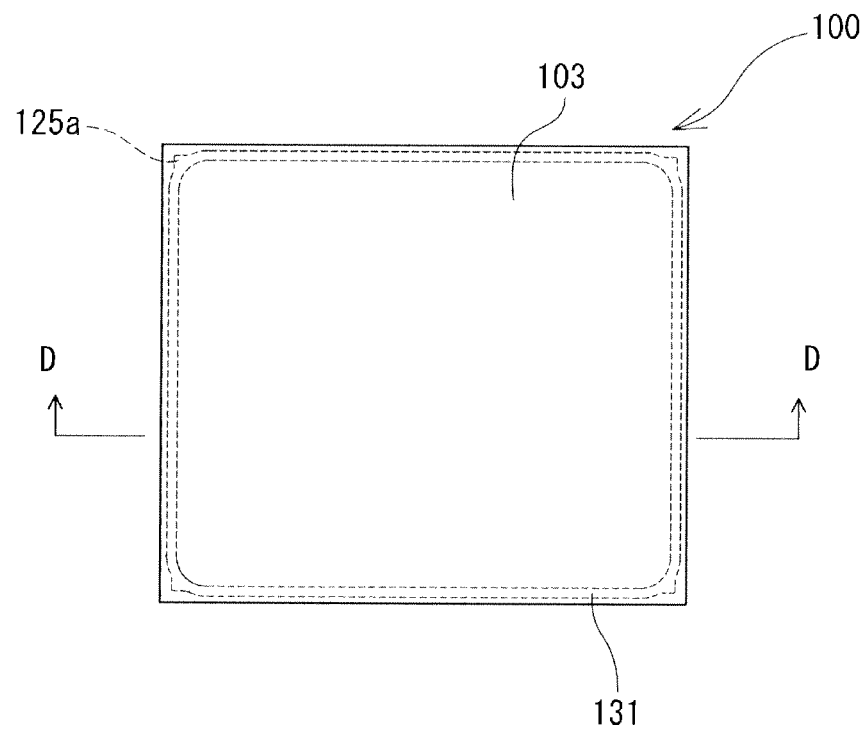
FIG. 14 is a plan view of the syringe assembly package body of FIG. 13.
Figure 15:
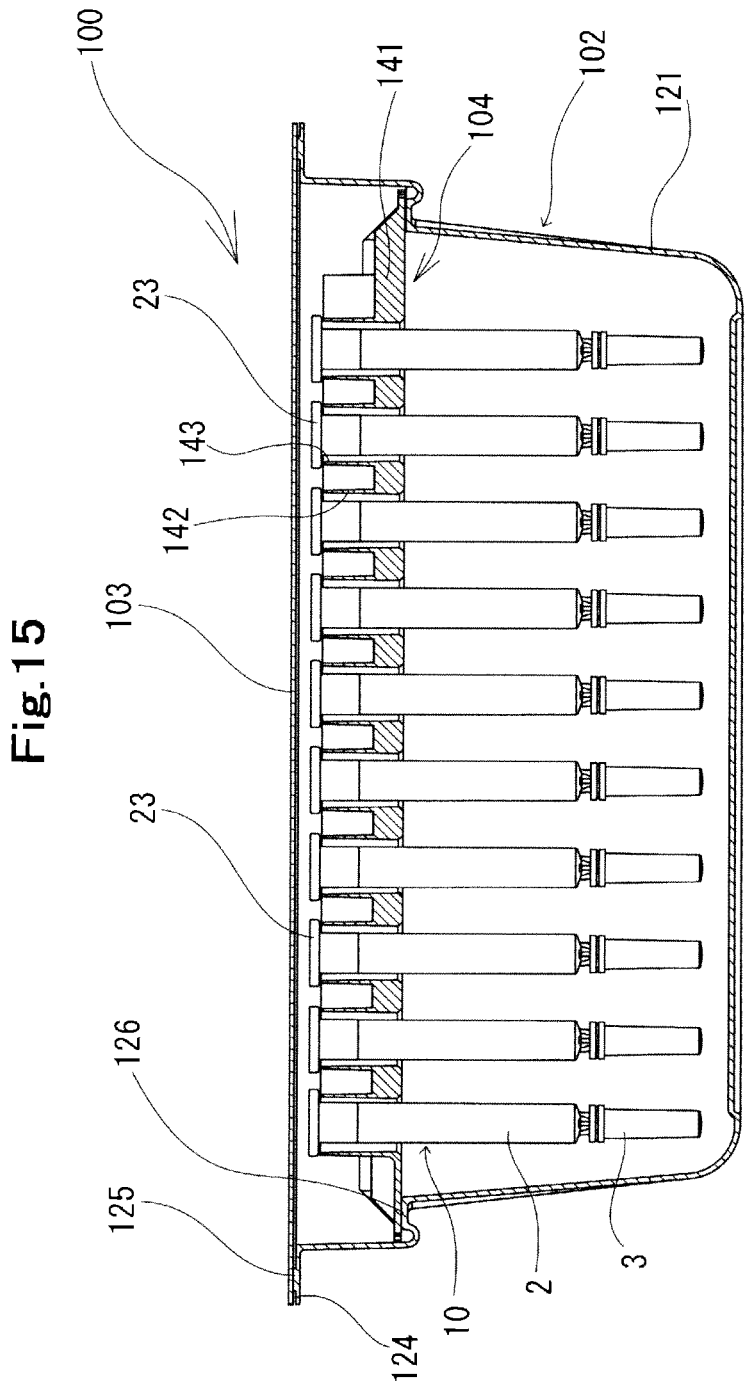
FIG. 15 is an enlarged cross-sectional view taken along line D-D of FIG. 14.

As illustrated in FIGS. 11, 12, and 15, the prefilled syringe assembly package body 100 according to this embodiment of the present invention includes the container body 102, the barrel holder 104 configured to hold the plurality of the syringe assemblies 10, the plurality of the syringe assemblies 10 held by the barrel holder 104, and the sheet-shaped lid member 103 configured to releasably hermetically seal the top opening of the container body 102. Further, the package body 100 includes a ventilation portion provided in the container body 102 or the sheet-shaped lid member 103, and having bacterial impermeability and a sterilization gas circulation property.

As illustrated in FIGS. 11 to 15, the container body 102 is formed into a tray shape having a predetermined depth to have a certain level of strength and shape retainability. The container body 102 includes a main body portion 121, a barrel holder holding portion 126, and an annular flange 124. The barrel holder holding portion 126 is formed at the upper part of the main body portion 121, and holds the peripheral edge of the barrel holder 104 holding the plurality of the syringe assemblies 10. The annular flange 124 is provided at the top opening.

Further, the annular flange 124 has an upper surface provided with an annular heat-sealing protrusion 125 for fixing the sheet-shaped lid member 103. The barrel holder holding portion 126 is formed at a position located on the bottom surface side away from the flange 124 by a predetermined length. In the container body 102 according to a first embodiment, the barrel holder holding portion 126 is formed as an annular stepped portion, and the peripheral edge of the barrel holder 104 holding the plurality of the syringe assemblies 10 can be mounted thereon.

The container body 102 preferably has a certain level of shape retainability and rigidity. Further, a thermoplastic material having heat resistance (120° C. or more) is preferably employed for high-pressure steam sterilization. A material having a certain level of shape retainability, rigidity, heat resistance, and thermal plasticity includes, for example, a polyolefin such as a polypropylene or a polyethylene, a vinyl chloride resin, a polystyrene/polypropylene resin, a polyethylene/ionomer (e.g., ethylene-based, styrene-based, fluorine-based)/polyethylene, a polyester resin (e.g., polyethylene terephthalate, polybutylene terephthalate, amorphous polyethylene terephthalate), PP/EVOH/PP (laminate). In this case, the thickness of the container body 102 is preferably approximately 0.05 to 4.00 mm, especially, 1.00 to 2.00 mm.

Further, the container body 102 may be configured to be subjected to the radiation or electron beam sterilization, and preferably uses a so-called radiation-resistant material. The radiation-resistant material (e.g., radiation-resistant polyolefin) can be used which has radiation resistance obtained by adding a hindered amine, and further an antioxidant, nucleating agent, or the like to a polyolefin (e.g., a polypropylene, a polyethylene). An example of the hindered amine includes bis(2,2,6,6-tetramethyl-piperidyl)sebacate, bis(2,2,6,6-tetramethyl-piperidinyl)adipate, bis(2,2,6,6-tetramethyl-piperidyl)fumarate, or the like. The antioxidant includes 1,1,3-tris(2-methyl-hydroxy-5-t-butylphenyl)butane, tris(3,5-di-T-butyl-4-hydroxybenzyl)isocyanurate, tetrakis[methylene-3-(3,5-di-t-butyl-4-hydroxyphenyl)propionate]-methane, or the like. An example of the nucleating agent includes 1,3,2,4-dibenzylidenesorbitol, 1,3,2,4-di(p-methyl-benzylidene)sorbitol, or the like.

As illustrated in FIGS. 12 and 15, the barrel holder 104 configured to hold the plurality of the syringe assemblies 10 includes a substrate portion 141, and a plurality of cylindrical portions 142 projecting upward from the substrate portion 141. A barrel holding opening portion 143 is formed in the cylindrical portion 142, and the substrate portion 141 has a side portion in which a grip notch portion 144 is formed. The cylindrical portion 142 and the barrel holding opening portion 143 have an inner diameter larger than the outer diameter of a maximum diameter portion of the syringe assembly 10 to be held, and not allowing the passage of a flange portion 23 of the syringe assembly 10 to be held.

Therefore, as illustrated in FIG. 15, the syringe assembly 10 penetrates cylindrical portion 142, and the syringe assembly 10 is suspended by the flange 23 from the barrel holding opening portion 143. As illustrated in FIG. 15, the lower end (distal end of the seal cap 3) of the syringe assembly 10 held by the barrel holder 104 does not make contact with the bottom surface of the container body 102. In other words, the bottom surface of the container body 102 and the lower end (distal end of the seal cap 3) of the syringe assembly 10 held by the barrel holder 104 are separated, and not obstructs circulation of steam. A material of the barrel holder 104 preferably includes heat resistance (120° C. or more) for high-pressure steam sterilization.

The sheet-shaped lid member 103 desirably includes a member having a sterilization gas circulation property, not passing microparticles such as bacteria or viruses, but passing a sterilization gas such as steam or ethylene oxide gas, for high-pressure steam sterilization or ethylene oxide gas sterilization. Further, the container body 102 is preferably configured to be heat-sealed. The sheet-shaped lid member 103 preferably employs, for example, a synthetic resin nonwoven fabric, specifically, a non-woven fabric including a synthetic resin material such as a polyolefin known as Tyvek (registered trademark), a synthetic resin porous membrane, or the like.

The sheet-shaped lid member 103 has a peripheral edge releasably heat-sealed to the heat-sealing protrusion 125 provided at the annular flange 124 of the container body 102. In the first embodiment, the outer edge of the sheet-shaped lid member 103 is not heat-sealed to the annular flange 124 of the container body 102, and the sheet-shaped lid member 103 is readily released. Further, a projection portion 125a provided at a corner of the heat-sealing protrusion 125 functions as a release start portion. The sheet-shaped lid member 103 is preferably has a thickness of approximately 0.05 to 1.00 mm, especially, approximately 0.10 to 0.50 mm.

In the first embodiment, the ventilation portion is provided in the sheet-shaped lid member 103, but the ventilation portion is not limited to this configuration, and may be provided in the container body 102.

In the prefilled syringe assembly package body 100, the syringe assembly 10 stored in the prefilled syringe assembly package body 100 is configured so that the inner surface of the barrel end storage portion 35 and the outer surface of the barrel end portion 22 are in close contact with each other through the non-stick surface 9. Therefore, when the prefilled syringe assembly package body 100 is stored while the seal cap 3 is mounted on the barrel 2, and when sterilization bringing about a pressure load, such as high-pressure steam sterilization or ethylene oxide gas sterilization, is performed on the prefilled syringe assembly package body 100, the sticking between the inner surface of the barrel end storage portion 35 and the outer surface of the barrel end portion 22 can be inhibited.

A syringe assembly according to an embodiment of the present invention includes the following.

(1) A syringe assembly including a barrel including a barrel body portion, a cylindrical barrel end portion provided at a distal end of the barrel body portion, the cylindrical barrel end portion having an annular head portion and an annular recessed portion formed at a proximal end of the annular head portion, and a puncture needle having a puncture needle tip at a distal end, the puncture needle having a proximal end fixedly inserted into the barrel end portion, and a seal cap mounted to the barrel, wherein the seal cap includes a closed distal end portion, an open proximal end portion, a hollow portion having a barrel end storage portion positioned distally from the open proximal end portion, the barrel end storage portion storing the barrel end portion, and a puncture needle storage portion extending from a distal end of the barrel end storage portion, the puncture needle storage portion storing the puncture needle, an insertion allowing portion for receiving the insertion of the puncture needle tip of the puncture needle stored in the puncture needle storage portion, and a projection portion formed on the inner surface of the barrel end storage portion, on the inner surface of the barrel end storage portion and/or the outer surface of the barrel end portion, a non-stick surface for inhibiting sticking between the inner surface of the barrel end storage portion and the outer surface of the barrel end portion is formed, and the seal cap is mounted to the barrel end portion of the barrel, the puncture needle tip is inserted into the insertion allowing portion of the seal cap, the projection portion of the seal cap and the annular recessed portion of the barrel end portion are engaged with each other, and the inner surface of the barrel end storage portion and the outer surface of the barrel end portion are in close contact with each other through the non-stick surface.

An embodiment of the syringe assembly may include the following.

(2) The syringe assembly according to (1), wherein the non-stick surface is formed by a coating of a non-stick substance and/or a surface treatment imparting non-adhesiveness to the inner surface of the barrel end storage portion and/or the outer surface of the barrel end storage portion.

(3) The syringe assembly according to (1), wherein the non-stick surface includes a non-stick polymer film.

(4) The syringe assembly according to (3), wherein the non-stick polymer film is a silicone polymer film formed from a liquid coating agent consisting primarily of a reactive silicone oil.

(5) The syringe assembly according to any of (1) to (4), wherein the projection portion includes a top portion, and a distal inclined portion extending distally from the top portion, and having a projection height gradually reduced distally, and the distal inclined portion is hermetically pressed against the outer surface of the annular head portion through the non-stick surface.

(6) The syringe assembly according to (5), wherein the distal inclined portion is hermetically pressed against the outer surface of the annular recessed portion through the non-stick surface.

(7) The syringe assembly according to (5) or (6), wherein the distal inclined portion has a portion hermetically pressed against the outer surface of the annular head portion, and the portion has a length in the axial direction of the annular head portion of 0.1 to 2.0 mm.

(8) The syringe assembly according to any of (5) to (7), wherein the projection portion has a proximal inclined portion extending from the top portion toward a proximal end, and having a projection height gradually reduced toward the proximal end.

(9) The syringe assembly according to any of (5) to (8), wherein the projection portion is the annular projection portion.

(10) The syringe assembly according to any of (1) to (9), wherein the non-stick surface is also formed on the inner surface of the puncture needle storage portion.

(11) The syringe assembly according to any of (1) to (10), wherein the annular recessed portion includes a tapered reduced diameter portion having a diameter reduced proximally.

(12) The syringe assembly according to any of (1) to (11), wherein the seal cap has a removal resistance from the barrel 2 of 1.5 to 20 N.

(13) The syringe assembly according to any of (1) to (12), wherein the hollow portion includes a barrel end introduction portion formed from the open proximal end portion to a proximal end of the barrel end storage portion, having an inner diameter larger than an outer diameter of the annular head portion, at least at a base end, and functioning as an introduction portion for the barrel end portion, upon mounting the seal cap to the barrel end portion of the barrel, and the non-stick surface is also formed on an inner surface of the barrel end introduction portion.

(14) The syringe assembly according to any of (1) to (13), wherein the syringe assembly is subjected to high-pressure steam sterilization or ethylene oxide gas sterilization.

A prefilled syringe according to an embodiment of the present invention includes the following.

(15) A prefilled syringe including the syringe assembly according to any of (1) to (14), a gasket stored in the barrel, and slidably moved in the barrel in a liquid-tight manner, and a medical solution filled in a space formed by the barrel and the gasket.

A seal cap for a barrel according to an embodiment of the present invention includes the following.

(16) A seal cap for a barrel, mounted to a barrel including a barrel body portion, a cylindrical barrel end portion provided at the distal end of the barrel body portion, the barrel end portion having an annular head portion and an annular recessed portion formed at the proximal end of the annular head portion, and a puncture needle having a puncture needle tip at the distal end, the puncture needle having a proximal end fixedly inserted into the barrel end portion, wherein the seal cap includes a closed distal end portion, an open proximal end portion, a hollow portion including a barrel end storage portion positioned distally from the open proximal end portion, the barrel end storage portion storing the barrel end portion, and a puncture needle storage portion extending from a distal end of the barrel end storage portion, the puncture needle storage portion storing the puncture needle, an insertion allowing portion for receiving the insertion of the puncture needle tip of the puncture needle stored in the puncture needle storage portion, and a projection portion formed on the inner surface of the barrel end storage portion, on the inner surface of the barrel end storage portion, a non-stick surface for inhibiting sticking to an outer surface of the barrel end portion is formed, when the seal cap is mounted to the barrel, the puncture needle tip is inserted into the insertion allowing portion of the seal cap, and when the projection portion and the annular recessed portion is engaged with each other, the inner surface of the barrel end storage portion and the outer surface of the barrel end portion are in close contact with each other through the non-stick surface.

An embodiment of the seal cap for a barrel may include the followings.

(17) The seal cap for a barrel according to (16), wherein the non-stick surface is formed by a coating of a non-stick substance and/or a surface treatment imparting non-adhesiveness to the inner surface of the barrel end storage portion.

(18) The seal cap for a barrel according to (17), wherein the non-stick surface includes the non-stick polymer film.

(19) The seal cap for a barrel according to (18), wherein the non-stick polymer film is a silicone polymer film formed from a liquid coating agent consisting primarily of a reactive silicone oil.

(20) The seal cap for a barrel according to any of (16) to (19), wherein the projection portion includes a top portion, and a distal inclined portion extending distally from the top portion, and having a projection height gradually reduced distally, and when the seal cap is mounted to the barrel, the distal inclined portion is hermetically pressed against the outer surface of the annular head portion through the non-stick surface.

(21) The seal cap for a barrel according to (20), wherein the projection portion has a proximal inclined portion extending from the top portion toward a proximal end, and having a projection height gradually reduced toward the proximal end.

(22) The seal cap for a barrel according to (20) or (21), wherein the projection portion is the annular projection portion.

(23) The seal cap for a barrel according to any of (16) to (22), wherein the non-stick surface is also formed on the inner surface of the puncture needle storage portion.

(24) The seal cap for a barrel according to any of (16) to (23), wherein the hollow portion includes a barrel end introduction portion formed from the open proximal end portion to a proximal end of the barrel end storage portion, having an inner diameter larger than an outer diameter of the annular head portion, at least at a proximal end, and functioning as an introduction portion for the barrel end portion, upon mounting the seal cap to the barrel end portion of the barrel, and the non-stick surface is also formed on an inner surface of the barrel end introduction portion.

A syringe assembly package body according to an embodiment of the present invention includes the following.

(25) A syringe assembly package body storing a plurality of the syringe assemblies according to any of (1) to (13), the package body including a container body having a top opening and having shape retainability, a barrel holder configured to hold a plurality of the syringe assemblies, a plurality of the syringe assemblies held by the barrel holder, and a releasable, sheet-shaped lid member configured to hermetically seal the top opening of the container body, the package body further including a ventilation portion provided in the container body or the lid member, and having bacterial impermeability and a sterilization gas circulation property, wherein the package body is subjected to high-pressure steam sterilization or ethylene oxide gas sterilization.

What is claimed is:
1. A syringe assembly comprising:
a barrel including:
a barrel body portion, a cylindrical barrel end portion disposed at a distal end of the barrel body portion, wherein the cylindrical barrel end portion including an annular head portion and an annular recessed portion formed at an outer surface of a proximal end of the annular head portion, and a puncture needle having a puncture needle tip at a distal end, the puncture needle having a proximal end fixedly disposed in the barrel end portion; and a seal cap mounted to the barrel, wherein the seal cap includes:

a closed distal end portion;

an open proximal end portion;

a hollow portion including a barrel end storage portion disposed distal of the open proximal end portion, the barrel end storage portion storing the barrel end portion, and a puncture needle storage portion extending from a distal end of the barrel end storage portion, the puncture needle storage portion storing the puncture needle;

an insertion allowing portion configured to receive the puncture needle tip of the puncture needle stored in the puncture needle storage portion; and a projection portion projecting inwardly from an inner surface of the barrel end storage portion of the hollow portion of the seal cap, wherein a non-stick surface for inhibiting sticking between the inner surface of the barrel end storage portion of the seal cap and an outer surface of the barrel end portion of the barrel is disposed on the inner surface of the barrel end storage portion of the seal cap, wherein the seal cap is mounted to the barrel end portion of the barrel, the puncture needle tip is disposed in the insertion allowing portion of the seal cap, the projection portion of the seal cap and the annular recessed portion of the barrel end portion are engaged with each other, and the non-stick surface is interposed between the inner surface of the barrel end storage portion of the seal cap and the outer surface of the barrel end portion, wherein the seal cap comprises a coating layer on the inner surface of the barrel end storage portion, the coating layer including the non-stick surface as an inner surface of the coating layer, and wherein the insertion allowing portion and the barrel end storage portion are formed from an elastic material, and the coating layer is formed from a non-stick substance different from the elastic material.

2. The syringe assembly according to claim 1, wherein the non-stick substance comprises a non-stick polymer film.

3. The syringe assembly according to claim 2, wherein the non-stick polymer film is a silicone polymer film formed from a liquid coating agent consisting essentially of a reactive silicone oil.

4. The syringe assembly according to claim 1, wherein the projection portion includes a top portion, and a distal inclined portion extending distally from the top portion and having a projection height gradually reduced distally, and the distal inclined portion is hermetically pressed against the outer surface of the annular head portion via the non-stick surface.

5. The syringe assembly according to claim 1, wherein the syringe assembly is high-pressure steam sterilized or ethylene oxide gas sterilized.

6. A prefilled syringe comprising:

the syringe assembly according to claim 1;

a gasket disposed in the barrel, and slidably movable in the barrel in a liquid-tight manner; and a medical solution filled in a space formed by the barrel and the gasket.

7. A seal cap for a barrel that includes (i) a barrel body portion, (ii) a cylindrical barrel end portion provided at the distal end of the barrel body portion, the barrel end portion having an annular head portion and an annular recessed portion formed at an outer surface of the proximal end of the annular head portion, and (iii) a puncture needle having a puncture needle tip at the distal end, the puncture needle having a proximal end fixedly disposed in the barrel end portion, the seal cap including:

a closed distal end portion;

an open proximal end portion;

a hollow portion including a barrel end storage portion disposed distal of the open proximal end portion, the barrel end storage portion being configured to store the barrel end portion of the seal cap, and a puncture needle storage portion extending from a distal end of the barrel end storage portion, the puncture needle storage portion being configured to store the puncture needle;

an insertion allowing portion configured to receive the insertion of the puncture needle tip of the puncture needle stored in the puncture needle storage portion; and a projection portion projecting inwardly from an inner surface of the barrel end storage portion of the hollow portion of the seal cap, wherein a non-stick surface for inhibiting sticking to an outer surface of the barrel end portion of the seal cap is formed on the inner surface of the barrel end storage portion, wherein, when the seal cap is mounted to the barrel, the puncture needle tip is disposed in the insertion allowing portion of the seal cap, and wherein, when the projection portion and the annular recessed portion are engaged with each other, the non-stick surface is interposed between the inner surface of the barrel end storage portion of the seal cap and the outer surface of the barrel end portion, and wherein the seal cap comprises a coating layer on the inner surface of the barrel end storage portion, the coating layer including the non-stick surface as an inner surface of the coating layer, and wherein the insertion allowing portion and the barrel end storage portion are formed from an elastic material, and the coating layer is formed from a non-stick substance different from the elastic material.

8. The seal cap for a barrel according to claim 7, wherein the non-stick substance comprises the non-stick polymer film.

9. The seal cap for a barrel according to claim 8, wherein the non-stick polymer film is a silicone polymer film formed from a liquid coating agent consisting essentially of a reactive silicone oil.

10. The seal cap for a barrel according to claim 7, wherein the projection portion includes a top portion, and a distal inclined portion extending distally from the top portion, and having a projection height gradually reduced distally, and when the seal cap is mounted to the barrel, the distal inclined portion is hermetically pressed against the outer surface of the annular head portion via the non-stick surface.

11. A syringe assembly package body storing a plurality of the syringe assemblies according to claim 1, the package body comprising:

a container body having a top opening and having shape retainability;

a barrel holder configured to hold a plurality of the syringe assemblies;

a plurality of the syringe assemblies held by the barrel holder; and a releasable, sheet-shaped lid member configured to hermetically seal the top opening of the container body, a ventilation portion disposed in the container body or the lid member, and having bacterial impermeability and a sterilization gas circulation property, wherein the package body is subjected to high-pressure steam sterilization or ethylene oxide gas sterilization.

12. A syringe assembly comprising:

a barrel including:
- a barrel body portion,
- a cylindrical barrel end portion disposed at a distal end of the barrel body portion, the cylindrical barrel end portion including an annular head portion and an annular recessed portion formed at an outer surface of a proximal end of the annular head portion, and
- a puncture needle having a puncture needle tip at a distal end, the puncture needle having a proximal end fixedly disposed in the barrel end portion; and a seal cap mounted to the barrel, wherein the seal cap includes:
- a closed distal end portion;
- an open proximal end portion;
- a hollow portion having a barrel end storage portion disposed distal of the open proximal end portion, the barrel end storage portion storing the barrel end portion, and a puncture needle storage portion extending from a distal end of the barrel end storage portion, the puncture needle storage portion storing the puncture needle;
- an insertion allowing portion configured to receive the puncture needle tip of the puncture needle stored in the puncture needle storage portion; and
- a projection portion projecting inwardly from an inner surface of the barrel end storage portion of the hollow portion of the seal cap, wherein a non-stick surface for inhibiting sticking between the inner surface of the barrel end storage portion of the seal cap and an outer surface of the barrel end portion of the barrel is disposed on the inner surface of the barrel end storage portion of the seal cap, wherein the seal cap is mounted to the barrel end portion of the barrel, the puncture needle tip is disposed in the insertion allowing portion of the seal cap, the projection portion of the seal cap and the annular recessed portion of the barrel end portion of the barrel are engaged with each other, and the non-stick surface is interposed between the inner surface of the barrel end storage portion of the seal cap and the outer surface of the barrel end portion, and wherein the non-stick surface comprises a treated surface formed by epoxidation or halogenation on the inner surface of the barrel end storage portion of the seal cap.

13. The syringe assembly according to claim 12, wherein the projection portion includes a top portion, and a distal inclined portion extending distally from the top portion and having a projection height gradually reduced distally, and the distal inclined portion is hermetically pressed against the outer surface of the annular head portion via the non-stick surface.

14. The syringe assembly according to claim 12, wherein the syringe assembly is high-pressure steam sterilized or ethylene oxide gas sterilized.

15. A prefilled syringe comprising:
the syringe assembly according to claim 12;
a gasket disposed in the barrel, and slidably movable in the barrel in a liquid-tight manner; and
a medical solution filled in a space formed by the barrel and the gasket.

16. The syringe assembly according to claim 1, wherein the puncture needle tip is configured to be inserted into the insertion allowing portion so as to be apart from the coating layer.

17. The syringe assembly according to claim 12, wherein the puncture needle tip is configured to be inserted into the insertion allowing portion so as to be apart from the coating layer.

18. The syringe assembly according to claim 1, wherein the annular head portion comprises a recess that is recessed proximally from a distal end surface of the annular head portion.

19. The syringe assembly according to claim 18, wherein the annular head portion comprises a hollow conical portion positioned in the recess.

20. The syringe assembly according to claim 12, wherein the annular head portion comprises a recess that is recessed proximally from a distal end surface of the annular head portion.

21. The syringe assembly according to claim 20, wherein the annular head portion comprises a hollow conical portion positioned in the recess.

* * * * *